(12) United States Patent
Liu

(10) Patent No.: US 7,056,301 B2
(45) Date of Patent: Jun. 6, 2006

(54) SYRINGE

(76) Inventor: Jung-O Liu, No. 51-9, Hsing Feng San Chuang, Chu Hsing Village, Tan Tsu Hsian, Taichung Hsien (TW)

( * ) Notice: Subject to any disclaimer, the term of this patent is extended or adjusted under 35 U.S.C. 154(b) by 0 days.

(21) Appl. No.: 10/928,274

(22) Filed: Aug. 30, 2004

(65) Prior Publication Data

US 2005/0054979 A1    Mar. 10, 2005

(30) Foreign Application Priority Data

Sep. 5, 2003   (CN) .............................. 03 1 57994
Oct. 8, 2003   (CN) ....................... 2003 1 0100718
Apr. 19, 2004  (CN) ..................... 2004 1 00350317

(51) Int. Cl.
*A61M 5/178* (2006.01)

(52) U.S. Cl. ............... 604/110; 604/240; 604/187; 604/228; 604/218

(58) Field of Classification Search ............... 604/110
See application file for complete search history.

(56) References Cited

U.S. PATENT DOCUMENTS 6,267,749 B1 *   7/2001   Miklos et al. ............. 604/110
6,361,525 B1 *   3/2002   Capes et al. ............... 604/240
6,391,008 B1 *   5/2002   Tsai ........................... 604/195
6,752,784 B1 *   6/2004   Tsai ........................... 604/110
2002/0193737 A1 * 12/2002   Popovsky ................... 604/110
2004/0024357 A1 *  2/2004   Pelkey et al. .............. 604/110
2004/0049160 A1 *  3/2004   Hsieh et al. ............... 604/195
2004/0153037 A1 *  8/2004   Huang ........................ 604/220

* cited by examiner

*Primary Examiner*—Nicholas D. Lucchesi
*Assistant Examiner*—Melissa A. McCorkle
(74) *Attorney, Agent, or Firm*—Bacon & Thomas PLLC

(57) ABSTRACT

A syringe, on which a needle member is mounted, includes a barrel, a plunger and a stopper. The barrel has a chamber, a stop portion adjacent to the needle member, a lock portion on a wall of the chamber and a needle mount. The plunger has a lock device and an operation portion for operation. A stopper has a stopper body to be squeezed into the chamber of the barrel for movement, a lock flange on the stopper body to be elastically deformed and to be locked with the lock portion of the barrel. The lock device is provided to the stopper body to be connected to the lock device of the plunger that connects the stopper to the plunger to move together. While the plunger is drawn, the lock device of the plunger or the stopper is broken and the stopper is restricted in the barrel.

5 Claims, 12 Drawing Sheets

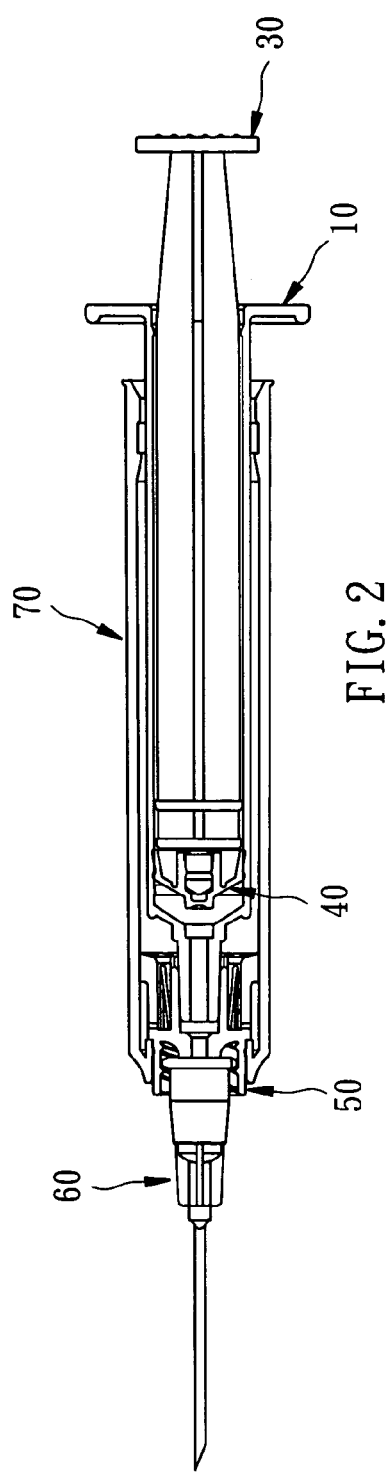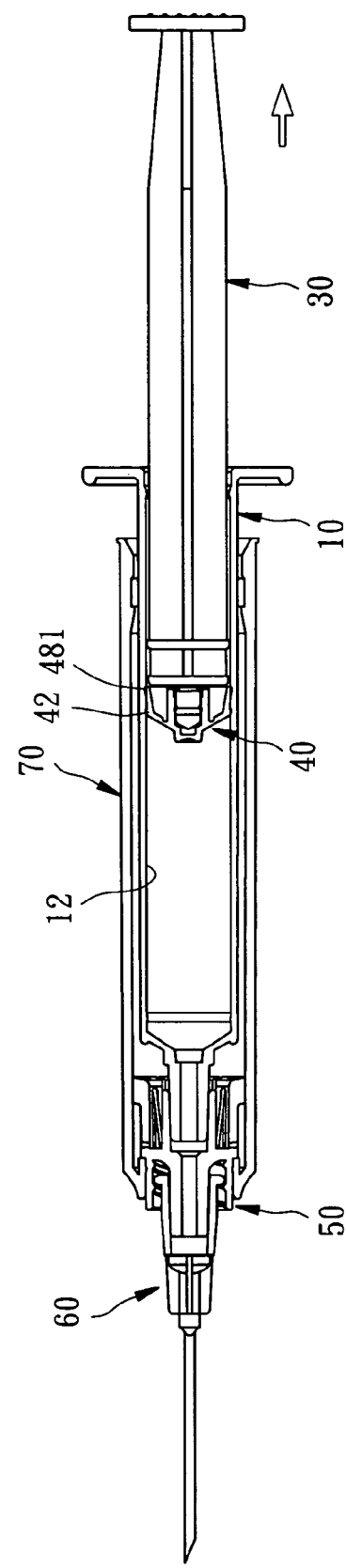

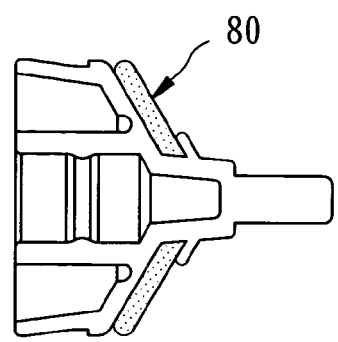
FIG. 14(A)
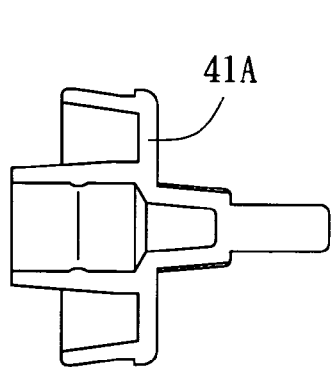 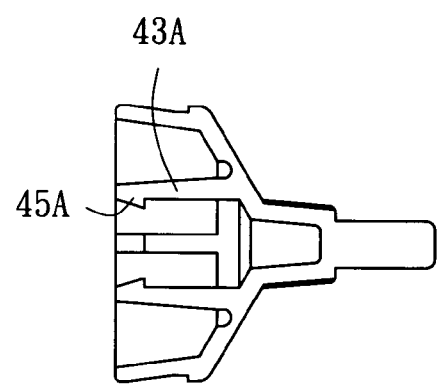
FIG. 14(B)  FIG. 14(C)
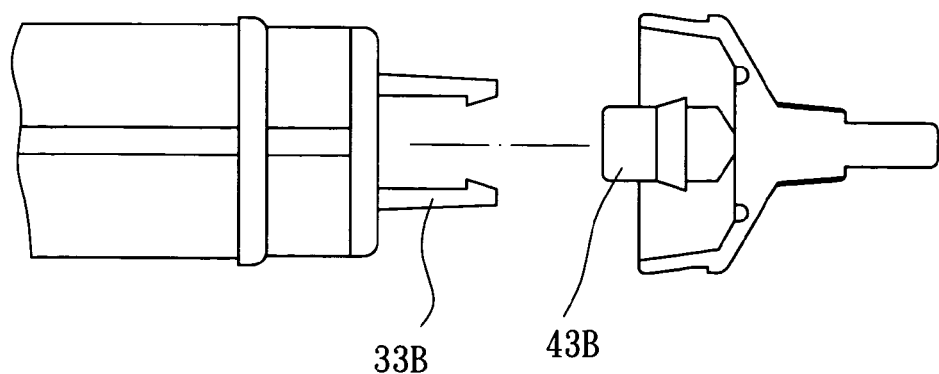
FIG. 15

US 7,056,301 B2

SYRINGE

BACKGROUND OF THE INVENTION

1. Field of the Invention

The present invention relates generally to a medical product, and more particularly to a syringe.

2. Description of the Related Art

To prevent patients from infection, the syringes are used for just one time. There are several types of syringes, which are destroyed after injection, provided in the present market. Some of the syringes are complex in structure, higher in cost or hard to operate and some of them can not provide a correct inject because the bad design or still can be used repeatedly. Such syringes are not broadly used in hospitals.

A conventional syringe still exposes the needle without any shield that might hurt people. To prevent aforesaid drawback, there are syringes, which the needle is shielded for protection. The conventional protective syringes usually have a complex structure and are hard to operate. In addition, they cannot be applied to the normal syringes. They have to redesign.

SUMMARY OF THE INVENTION

The primary objective of the present invention is to provide a syringe, which the needle is restricted in the barrel to prevent it from reuse.

The secondary objective of the present invention is to provide a syringe, which is easy in fabrication, assembly and operation.

The third objective of the present invention is to provide a syringe, which provides a simple structure and an easy operation to draw the needle into the barrel for safety.

According to the objectives of the present invention, a syringe adapted to mount a needle member thereon, comprises a barrel having a barrel body, in which a chamber is formed, a stop portion formed on the barrel body adjacent to the needle member, a lock portion formed on a wall of the chamber and a needle mount to be connected to the needle member. A plunger has a plunger rod, a lock device provided at the plunger rod and an operation portion at a rear end of the plunger rod for operation by fingers. A stopper has a stopper body, which is a round disk to be squeezed into the chamber of the barrel for movement, a lock flange formed on the stopper body to be elastically deformed and to be moved forward to pass the lock portion of the barrel and locked by the lock portion while it is moved backward. A lock device is provided to the stopper body to be connected to the lock device of the plunger that connects the stopper to the plunger to move together. While the plunger is drawn, the lock device of the plunger or the lock device of the stopper is able to be broken and the stopper is received and restricted in the barrel to prevent the syringe form reuse.

BRIEF DESCRIPTION OF THE DRAWINGS

FIG. 2 is a sectional view of the first preferred embodiment of the present invention in combination;

FIG. 3 is a sectional view of the first preferred embodiment of the present invention, showing the plunger being drawn;

FIG. 14(A), FIG. 14(B), and FIG. 14(C) shows three alternative stoppers;

FIG. 15 shows another alternative stopper and the plunger;

DETAILED DESCRIPTION OF THE INVENTION

Figure 1:
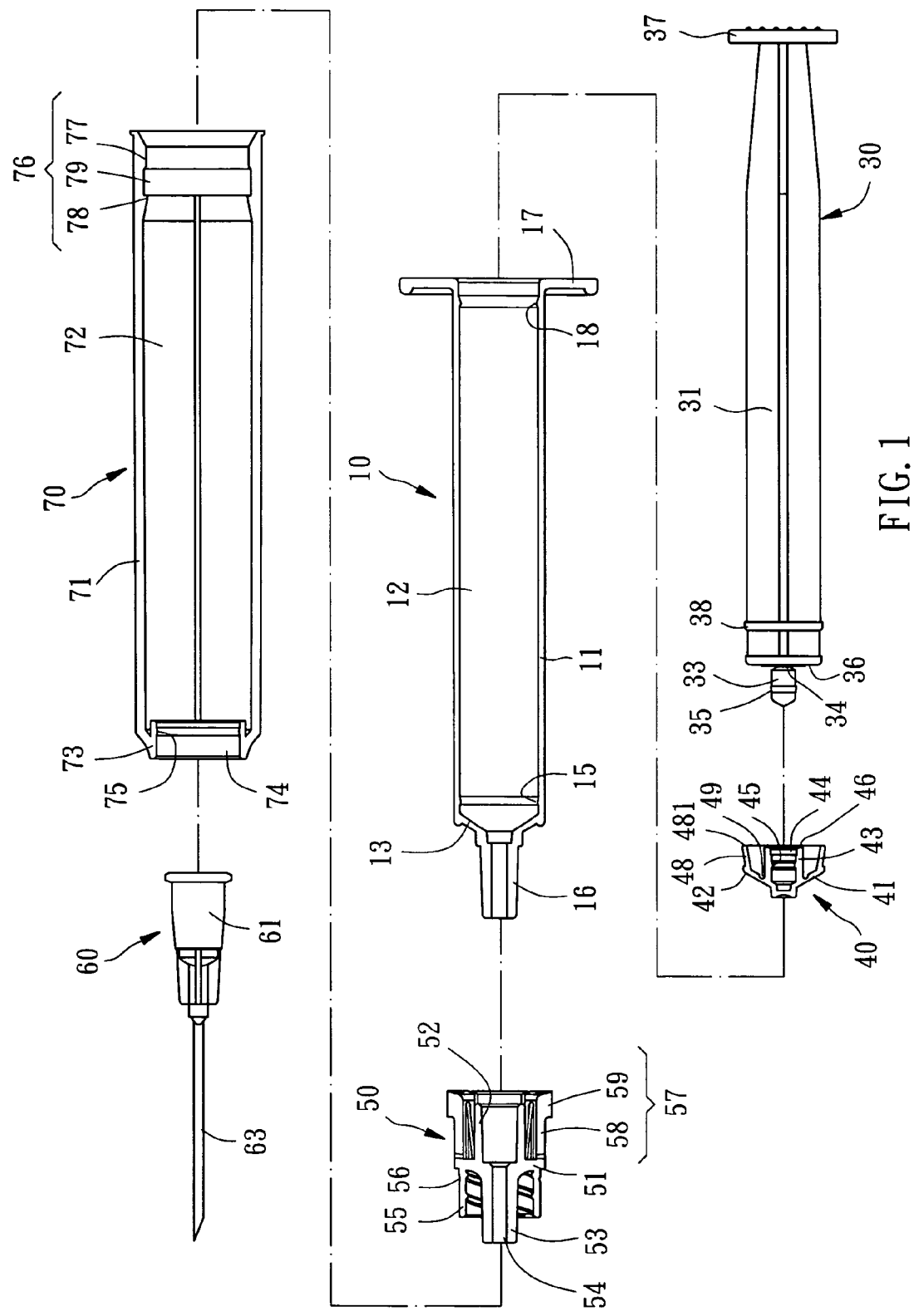
FIG. 1 is an exploded view of a first preferred embodiment of the present invention.

As shown in FIGS. from FIG. 1 to FIG. 7, a syringe of the first preferred embodiment of the present invention is to mount a needle member 60, which has connector portion 61 and a needle 63 mounted to the connector portion 61.

The syringe of the first preferred embodiment of the present invention comprises:

A barrel 10 has a barrel body 11 in which a chamber 12 is formed, a stop portion 13 formed on the barrel body 11 adjacent to the needle member 60, a lock portion 15 formed on an inner end a wall of the chamber 12 beside the stop portion 13, a needle connector 16 provided at a front end of the barrel body 11, a holding flange 17 provided at a rear end of the barrel body 11 and a plunger stop lip 18 formed on an outer end of the wall of the chamber 12 adjacent to an opening thereof.

A plunger 30 has a plunger rod 31 to be inserted into the chamber 12 of the barrel 10, a lock device 33 provided at a forward end of the plunger rod 31, a break portion 34 formed between the plunger rod 31 and the lock device 33, a hook portion 35 formed on an exterior side of the lock device 33, a resting portion 36 at a front end of the plunger rod 31, an operating portion 37 at a rear end of the plunger rod 31 for operation by fingers and a restriction portion 38 to be against the plunger stop lip 18 of the barrel 10.

A stopper 40 is made of polyethylene (PE) and is made by mold injection. The stopper 40 has a stopper body 41, which is a flexible round cone disk, a lock flange 42 formed and an exterior side of the stopper body 41, a lock device 43 provided on the stopper body 41 and facing the plunger 30, a lock hole 44 formed in the lock device 43, a hook portion 45 formed in the lock hole 44 to be connected to the hook portion 35 of the plunger 30 and a resting portion 46 to be attached on the resting portion 36 of the plunger 30. The lock flange 42 can cross the lock portion 15 of the barrel 10 and is locked by the lock portion 15. In the first preferred embodiment, the lock flange 42 seals the chamber 12 of the barrel 10.

The stopper 40 further has a flexible balancer 48 connected to the stopper body 41. The balancer 48 has a balance flange 481 pressing the wall of the chamber 12 of the barrel 10 to provide the chamber 12 an airtight condition and an annular slot 49 at an interior side of the stopper body 41. The slot 49 makes the stopper body 41 easier to be deformed.

A needle mount 50 has a mount 51, a barrel connector 52, which has a hole to be engaged with the needle connector 16 of the barrel 10, a through hole 54, an outer barrel connector 55 on an interior side of which a thread is provided to be engaged with the needle member 60, a positioning potion 56, which is an annular recess and an outer barrel lock portion 57 having three elastic plates 58 and on each of which a block 59 is provided at an end respectively.

An outer barrel 70 has a barrel body 71, a connector hole 72, a needle mount connector 73 to receive the outer barrel connector 55 of the needle mount 50 therein, a positioning portion 75, which is an annular lip to be acted with the positioning portion 56 of the needle mount 50 for positioning and stabilization and a needle mount lock portion 76 having two blocks 77 and 78 and a slot 79 between the blocks 77 and 78.

The way of operating the syringe of the present invention is described hereunder:

As shown in FIG. 3, the plunger 30 is drawn to suck fluid in the chamber 12 of the barrel 10. The balance flange 481 of the balancer 48 attached on the wall of the chamber 12 of the barrel 10 to balance the stopper 40.

Figure 4:
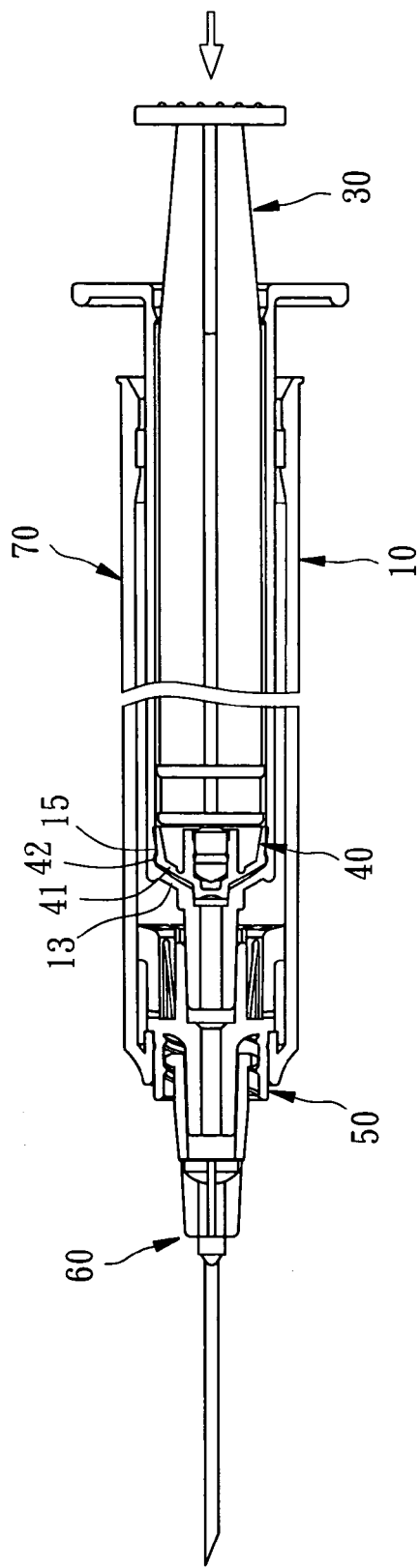
FIG. 4 is a sectional view of the first preferred embodiment of the present invention, showing the plunger being pushed.

As shown in FIG. 4, the plunger 30 is pushed inward and attaches the resting portion 36 thereof on the resting portion 46 of the stopper 40. The lock flange 42 of the stopper 40 is compressed to be deformed by the lock portion 15 of the barrel 10 and passes it. And then, the plunger 30 is pushed further to the end of the chamber 12 to drive the stopper body 41 of the stopper 40 pressing the stop portion 13 of the barrel 10. The fluid in the chamber 12 is injected out.

Figure 5:
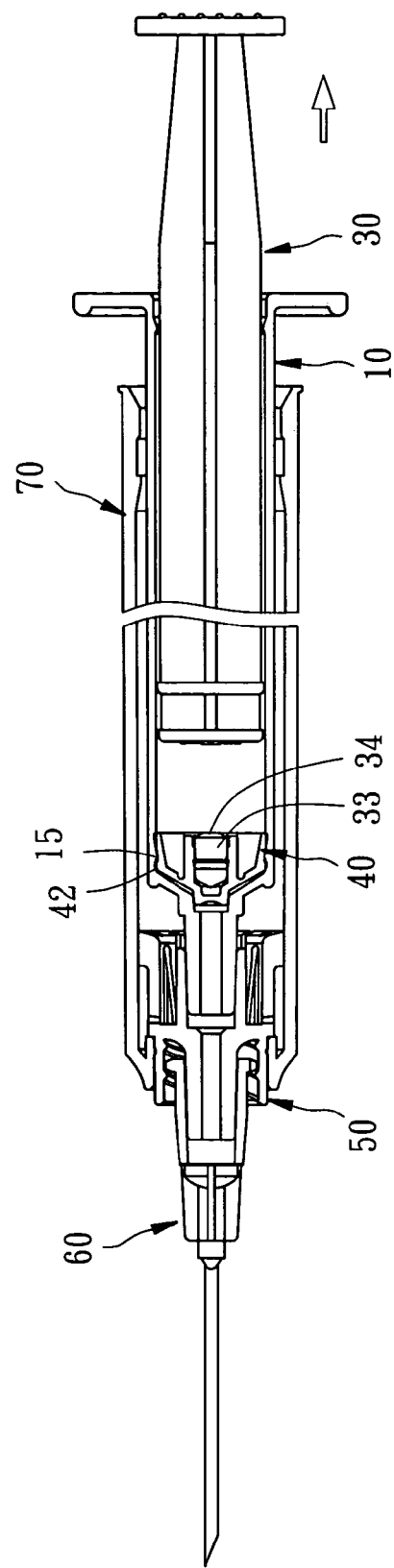
FIG. 5 is a sectional view of the first preferred embodiment of the present invention, showing the plunger being drawn and broken.

While drawing the plunger 30, the lock flange 42 of the stopper 40 is stopped by the lock portion 15 of the barrel 10 and the plunger 30 is broken at the break portion 34 between the plunger rod 31 and the lock device 33 to disengage the plunger rod 31 from the stopper 40. In such condition, the lock device 33 and the stopper 40 remain in the chamber 12 of the barrel 10 and are restricted therein, as shown in FIG. 5. The syringe is destroyed and can not be reused again.

Figure 6:
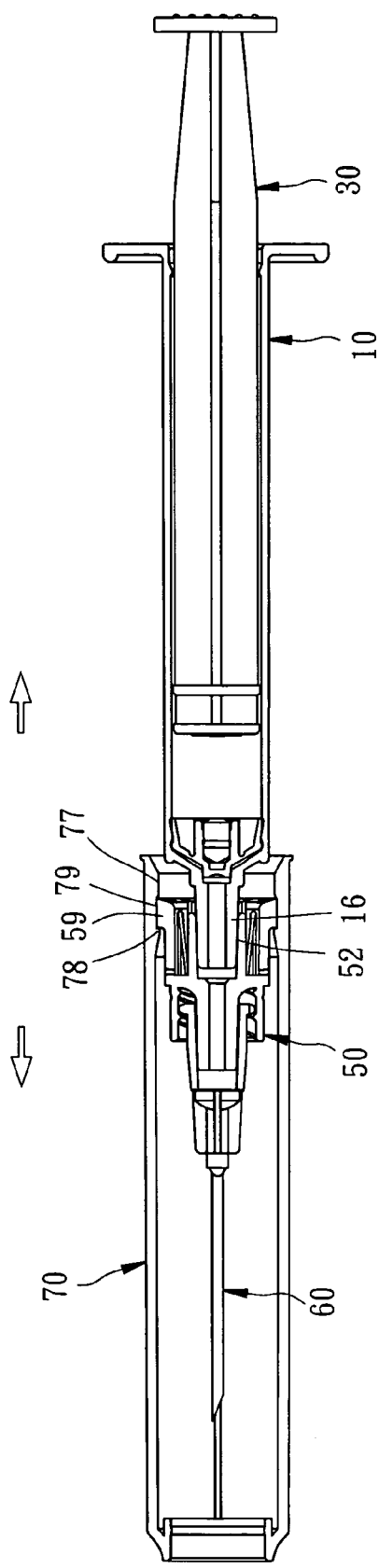
FIG. 6 is a sectional view of the first preferred embodiment of the present invention, showing the outer barrel being mounted.
Figure 7:
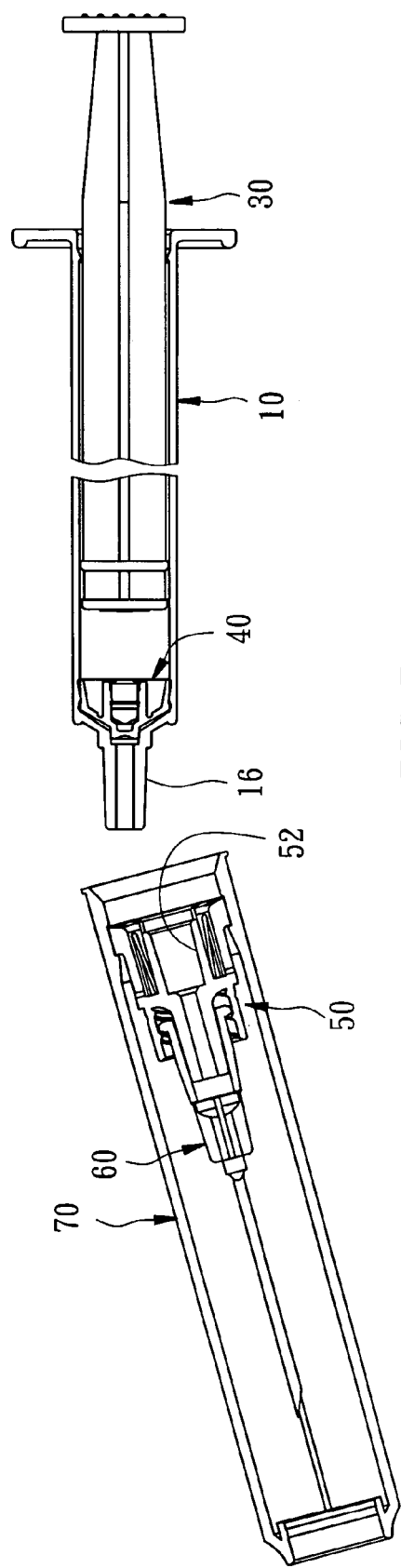
FIG. 7 is a sectional view of the first preferred embodiment of the present invention, showing the outer barrel being removed.

As shown in FIG. 6, the barrel 10 and the outer barrel 70 are pulled for separation. The needle mount 50 is moved with the barrel 10 and is separated from the needle mount connector 73 of the outer barrel 70. At last, the block 59 of the outer barrel lock portion 57 of the needle mount 50 is locked with the needle mount lock portion 76 of the outer barrel 70 and the needle member 60 is still connected to the needle mount 50 and is received in the connector hole 72 of the outer barrel 70, as shown in FIG. 7. The needle member 60 is restricted in the outer barrel 70 that protect people from hurt.

The syringe of the present invention serves both functions of self-destroy to prevent it from reuse and restricting the needle in the barrel to prevent it from hurting people.

It has to be mentioned that the syringe of the present invention should not be restricted to the self-destroy syringe as described above. The any type of self-destroy syringe with, for example stopper or plunger, can be applied to the syringe of the present invention with the functions of self-destroy and restricting the needle in the barrel.

Figure 8:
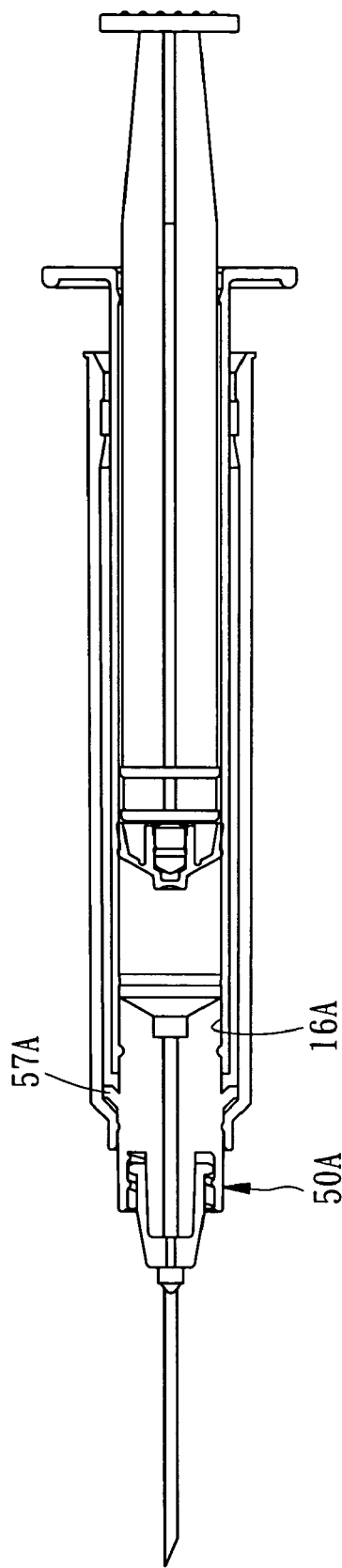
FIG. 8 is a sectional view of a second preferred embodiment of the present invention, showing the needle mount being mounted in the barrel.

There are some alternated structures of the syringe of the present invention and they are described hereunder:

As shown in FIG. 8, a needle mount 50A is mounted in a hole of a needle mount 16A at a front end of a barrel rather than it is fitted to the barrel. An outer barrel lock portion 57A is molded on the needle mount 50A directly to be locked with the needle mount lock portion of the outer barrel.

Figure 9:
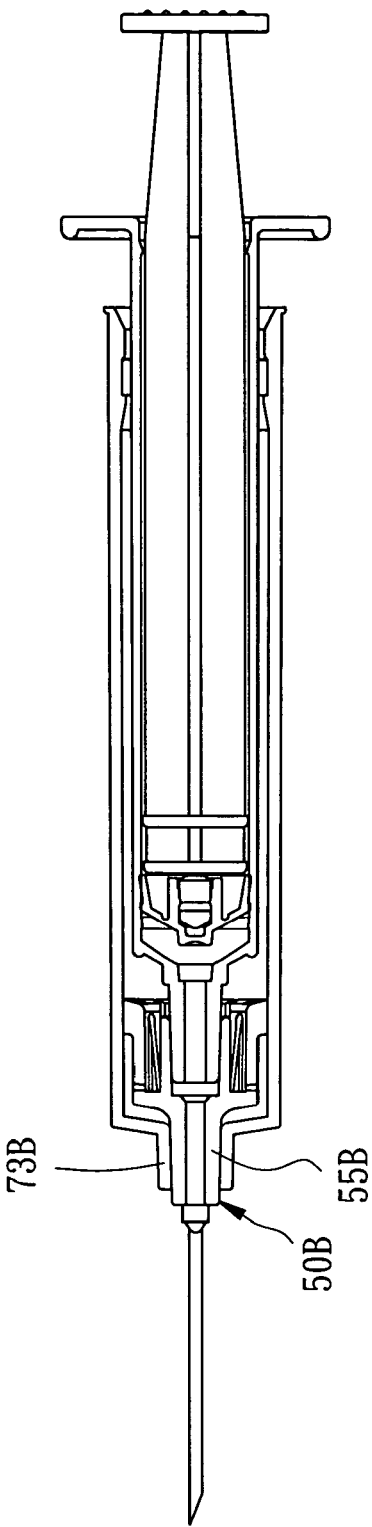
FIG. 9 is a sectional view of a third preferred embodiment of the present invention, showing the needle being mounted to the needle mount directly.

As shown in FIG. 9, the needle of the needle member is mounted to a needle mount 50B directly. An outer barrel connector 55B of the needle mount 50B and a needle mount connector 73B of the outer barrel have different shapes to be fitted together. For the same principle, the needle of the needle member is mounted to the needle mount 50A directly.

In addition, the outer barrel lock portion of the needle mount can be an independent component rather then molded on the needle mount.

Figure 10:
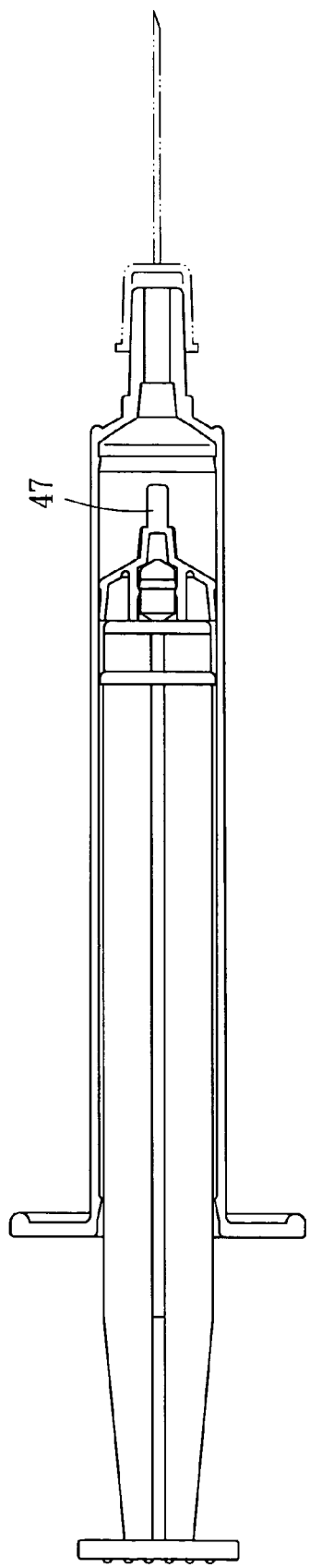
FIG. 10 is a sectional view of the third preferred embodiment of the present invention, showing the extended bar.
Figure 11:
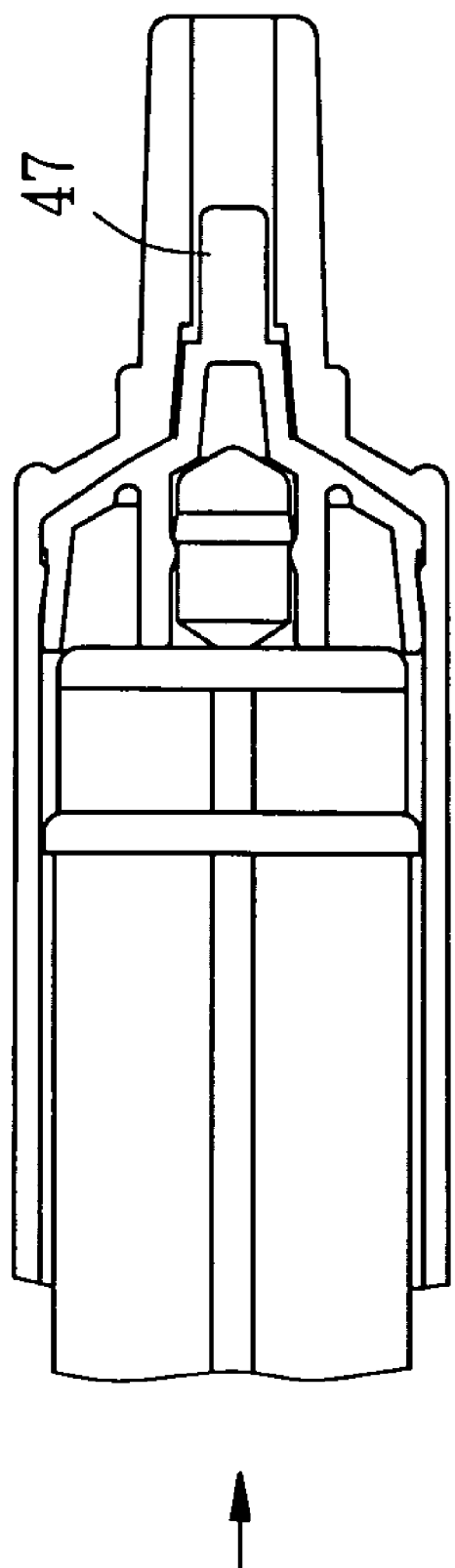
FIG. 11 is a sectional view in part of the third preferred embodiment of the present invention in combination.

As shown in FIG. 10, it shows a barrel of the present invention with no outer barrel. Furthermore, the syringe provides an extended bar 47 on the front end of the stopper. FIG. 11 shows that they are fitted to each other.

Figure 12:
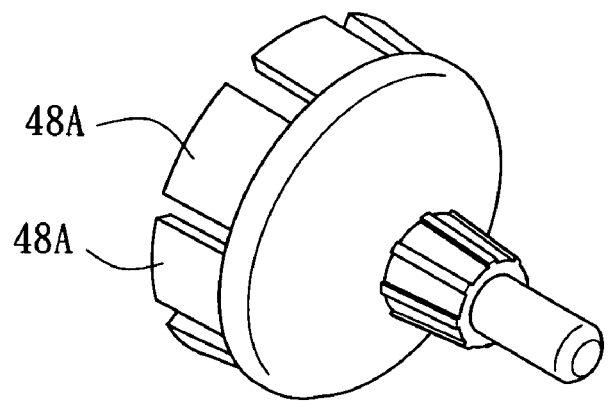
FIG. 12 is a perspective view of another stopper.

FIG. 12 shows the balancer having a plurality of balance plates 48A arranged in an average distribution.

Figure 13:
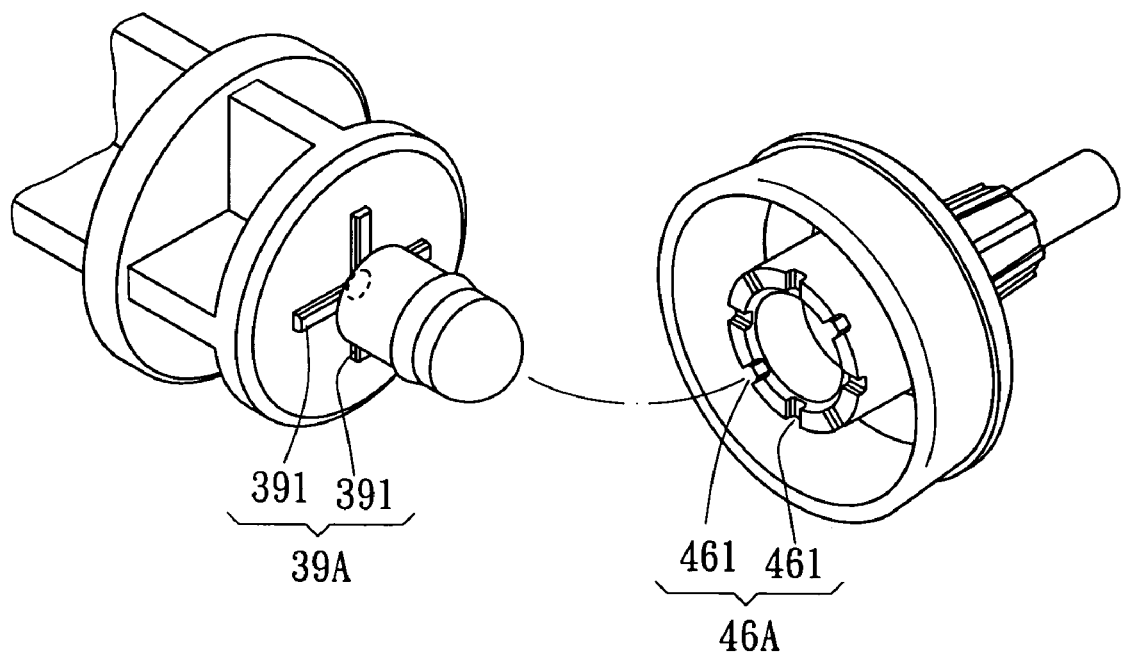
FIG. 13 is a perspective view of the third type of the stopper and the plunger.

As shown in FIG. 13, the plunger further has a rotation lock portion 39A, on which a plurality of ribs 391 are provided. The stopper has a rotation lock portion 46A, on which a plurality of slots 461 are provided. They are engaged with each other to prevent the plunger from rotation relative to the stopper that prevents the plunger from being twisted to break the break portion 34.

The alternated structures of the stopper and the plunger are shown in FIG. 14(A)–FIG. 14(C) and in the FIG. 15. The syringe further comprise a rubber sealer 80, the stopper body 41A of the stopper is flat, another type of the lock device 43A and hook portion 45A of the stopper, or another lock device 33B and lock device 43B.

Figure 16:
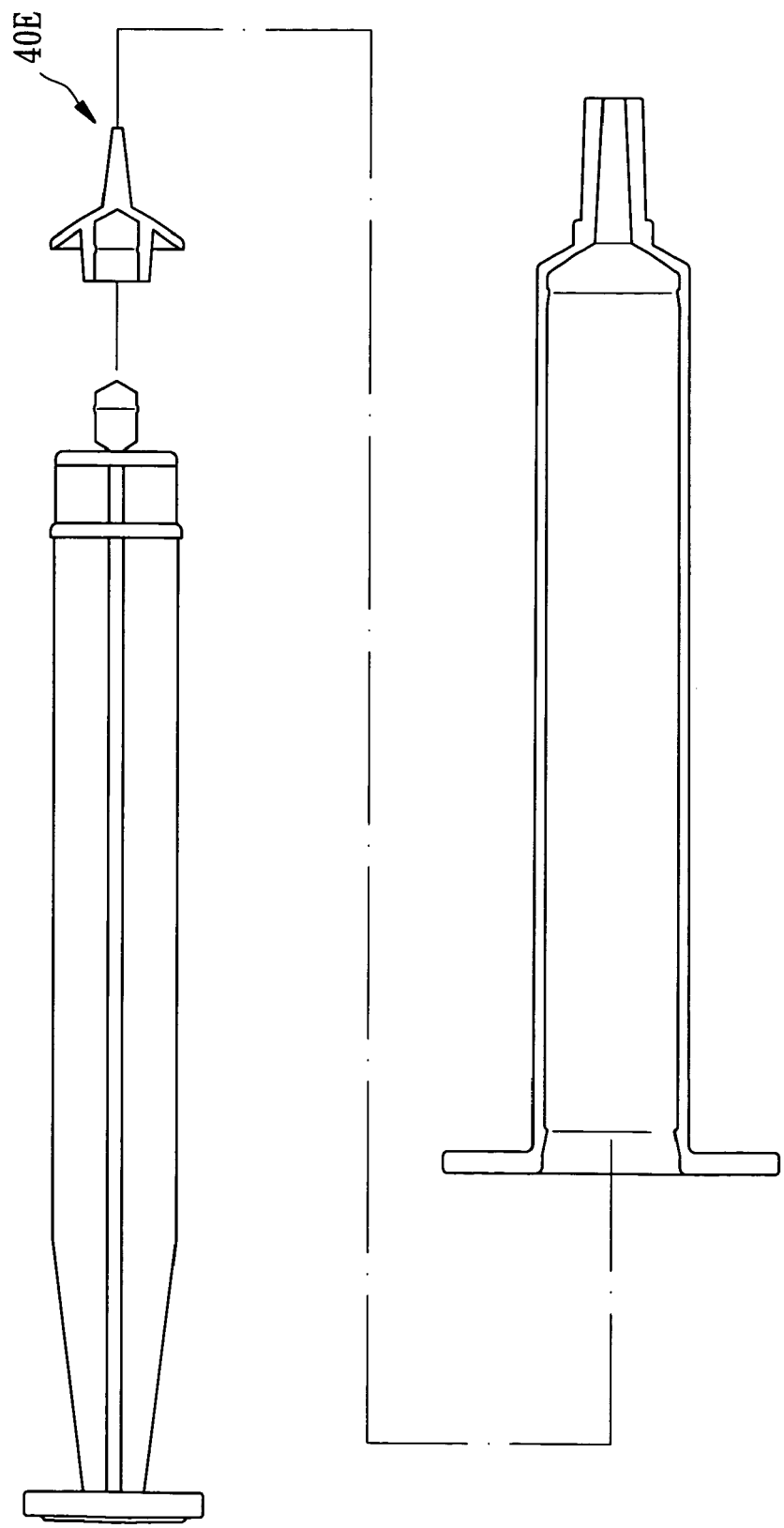
FIG. 16 is an exploded view of a simplified embodiment.
Figure 17:
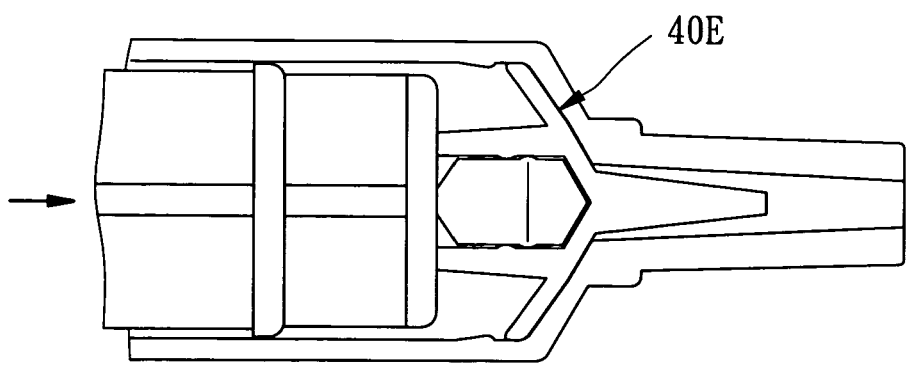
FIG. 17 is a sectional view of the simplified embodiment in combination.
Figures 18A, 18B:
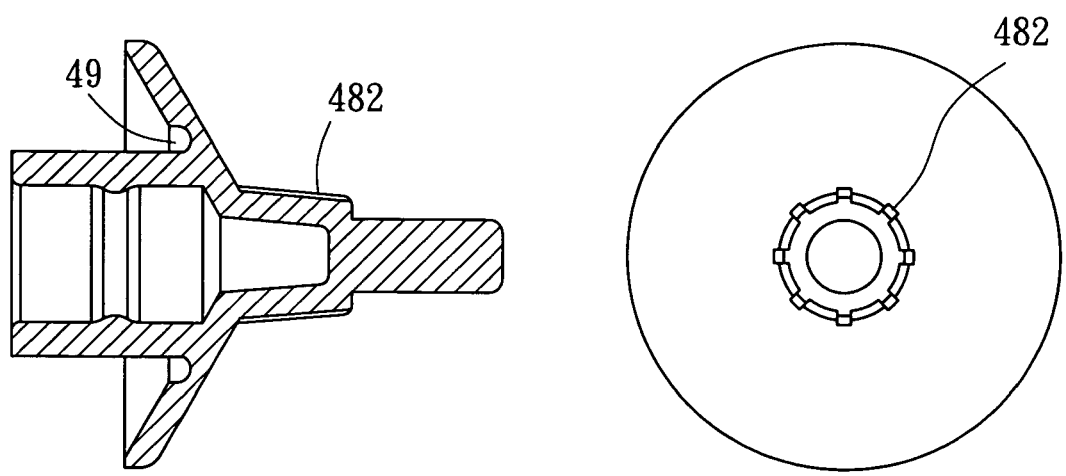
FIG. 18(A) and FIG. 18(B) shows two stoppers of the simplified embodiment.
Figure 19A:
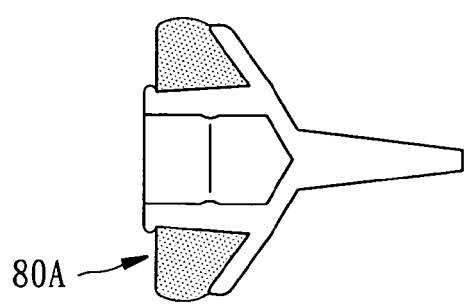
FIG. 19(A), FIG. 19(B), FIG. 19(C), and FIG. 19(D) shows four stoppers of the simplified embodiment.
Figure 19B:
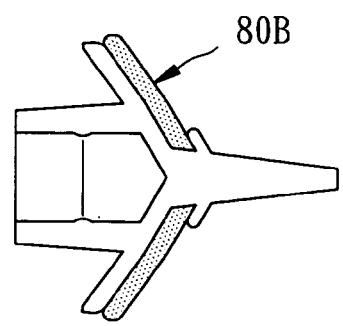
Figure 19C:
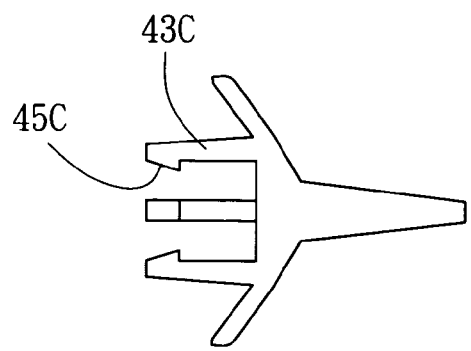
Figure 19D:
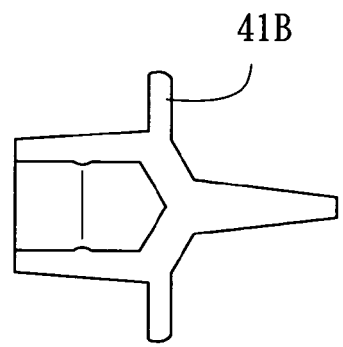
Figure 20:
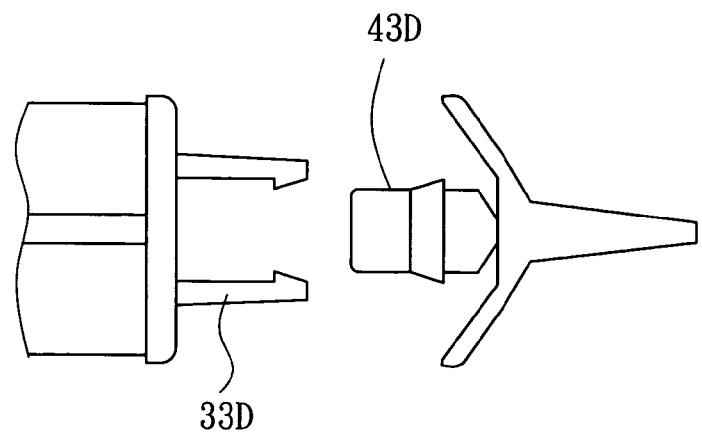
FIG. 20 shows the stopper and the plunger.

FIG. 16 and FIG. 17 show a syringe that a stopper 40E is provided with no balancer and balance flange. FIG. 18(A) and FIG. 18(B) show the stopper is provided with a rib 481 and an annular slot 49.

Four alternated stoppers are shown in FIG. 19(A)–FIG. 19(D) and FIG. 20 shows an alternated stopper adapted to be fitted to a plunger. Two kind of the rubber sealer 80A and 80B, another type of the lock device 43C and hook portion 45C of the stopper, the stopper body 41B of the stopper is flat, or another lock device 33D and lock device 43D.

The features of the present invention are:

1. The syringe of the present invention restricts the stopper in the barrel to prevent it from reuse.

2. The syringe of the present invention provides the stopper and the plunger having simpler structure for connection and disconnection. It has a lower cost of fabrication and an easier way of operation.

3. The syringe of the present invention provides a simple structure and an easy way of operation. The needle is drawn into the barrel to prevent people from hurt.

What is claimed is:

1. A syringe adapted to mount a needle member thereon, comprising:

a barrel having a barrel body in which a chamber is formed, a stop portion formed on said barrel body adjacent to said needle member, a lock portion formed on a wall of said chamber and a needle mount to be connected to said needle member, a plunger having a plunger rod, a lock device provided at a forward end of said plunger rod and an operation portion at a rear end of said plunger rod for operation by fingers;

a stopper having a stopper body, which is a round disk to be squeezed into said chamber of said barrel for movement, a lock flange formed on said stopper body to be elastically deformed and to be moved forward to pass said lock portion of said barrel and to be locked by said lock portion while it is moved backward and a lock device provided to said stopper body to be connected to said lock device of said plunger that connects said stopper to said plunger to move together, wherein while said plunger is drawn, said lock device of said plunger or said lock device of said stopper is able to be broken to disengage the plunger rod from the stopper, and said stopper is received and restricted in said barrel to prevent said syringe from reuse and wherein said stopper further has a balancer connected to said stopper body, which is flexible to be compressed for deformation, and a circular balance flange pressing said wall of said chamber of said barrel.

2. The syringe as defined in claim 1, wherein said plunger has a break portion between said plunger rod and said lock device.

3. The syringe as defined in claim 1, further comprising an outer barrel with a barrel body, a connector hole to be fitted to said barrel body of said barrel and a needle mount lock portion provided at a rear section, wherein said needle mount has an outer barrel lock portion and said while said barrel is moved away from said outer barrel, said needle mount is moved along with said barrel and said needle mount is engaged with said needle mount lock portion of said outer barrel whereby said needle member is received in said connector hole of said outer barrel and said needle mount lock portion is disconnected with said needle mount.

4. The syringe as defined in claim 3, wherein said needle mount has an outer barrel connector and said outer barrel has a needle mount connector to receive said outer barrel connector of said needle mount.

5. The syringe as defined in claim 4, wherein said needle mount further has a positioning portion and said outer barrel has a positioning portion to be engaged with said positioning portion of said needle mount.

* * * * *